United States Patent [19]

Dewald

[11] 4,329,524
[45] May 11, 1982

[54] SEPARATION OF 3,5-DICHLOROCUMENE FROM A MIXTURE OF 3,5-DICHLOROCUMENE AND 2,4-DICHLOROCUMENE

[75] Inventor: James R. Dewald, Bay City, Mich.

[73] Assignee: The Dow Chemical Company, Midland, Mich.

[21] Appl. No.: 129,514

[22] Filed: Mar. 12, 1980

Related U.S. Application Data

[63] Continuation-in-part of Ser. No. 51,091, Jun. 22, 1979, abandoned, which is a continuation-in-part of Ser. No. 903,423, May 8, 1978, abandoned.

[51] Int. Cl.$^3$ ............................................. C07C 17/38
[52] U.S. Cl. .................................................... 570/190
[58] Field of Search ..................... 260/650 R; 570/190

[56] References Cited

U.S. PATENT DOCUMENTS 3,345,423 10/1967 Tolgyesi .................... 260/650 R
3,358,046 12/1967 Offenhauer et al. ............ 260/650 R
3,553,274 1/1971 Lewis et al. .................... 260/650 R
4,059,642 11/1977 Dewald et al. ................ 260/650 R Primary Examiner—Delbert E. Gantz
Assistant Examiner—Joseph A. Boska
Attorney, Agent, or Firm—S. Preston Jones; Ronald G. Brookens

[57] ABSTRACT 3,5-Dichlorocumene is separated from a mixture comprising 3,5-dichlorocumene and 2,4-dichlorocumene by a process comprising contacting the mixture with an isopropyl group acceptor, in the presence of a catalyst comprising:
  (1) at least one Lewis acid compound, and
  (2) a proton source.

The isopropyl group of 2,4-dichlorocumene is preferentially transferred, as compared to the isopropyl group of 3,5-dichlorocumene, to the acceptor forming a reaction product comprising an acceptor bearing the isopropyl group, 3,5-dichlorocumene and m-dichlorobenzene. 3,5-Dichlorocumene is readily separated from this reaction product by any conventional technique, typically distillation.

7 Claims, No Drawings

SEPARATION OF 3,5-DICHLOROCUMENE FROM A MIXTURE OF 3,5-DICHLOROCUMENE AND 2,4-DICHLOROCUMENE

CROSS-REFERENCE TO RELATED APPLICATION

This is a continuation-in-part of copending application Ser. No. 051,091, filed June 22, 1979, now abandoned, which in turn is a continuation-in-part of application Ser. No. 903,423, filed May 8, 1978, now abandoned.

FIELD OF THE INVENTION

This invention relates to a process for separating 3,5-dichlorocumene from a mixture of 3,5- and 2,4-dichlorocumene.

BACKGROUND OF THE INVENTION

Mixtures of 3,5- and 2,4-dihalo-1-alkylbenzenes and especially mixtures containing 3,5-dichlorocumene and 2,4-dichlorocumene are readily prepared by reacting a m-dihalobenzene with an alkylating agent in the presence of an aluminum chloride Friedel-Crafts catalyst as taught in Dreisbach et al., U.S. Pat. No. 2,186,960. However, such mixtures, especially isomeric mixtures, are difficult to separate by conventional separatory procedures because of like physical properties. For example, separation of many isomeric mixtures by distillation is extremely difficult, if not impossible, because the boiling points of many of the individual components are almost identical.

In view of the severe difficulties existent in the conventional processes for preparing and separating such compounds from isomeric mixtures thereof, it would be highly desirable to provide an improved process for separating such isomers.

Such separation procedures can be found in Dewald and Markley, U.S. Pat. No. 4,059,642 and U.S. Pat. No. 4,104,315, which teach processes which comprise contacting an isomeric mixture of ar-dihalo-ar-alkylbenzenes with an alkylating agent in the presence of a Friedel-Crafts catalyst at a reaction temperature less than about 90° C. such that the isomer having substituents in the 1,2,4-ring positions is preferentially alkylated. The alkylated isomer is then readily separated from the remaining unreacted isomer by simple distillation. While these procedures are effective, other procedures are still being sought.

SUMMARY OF THE INVENTION

According to the present invention, 3,5-dichlorocumene is separated from a mixture comprising 3,5-dichlorocumene and 2,4-dichlorocumene in a process which comprises:
  (a) contacting the said mixture with an isopropyl group acceptor, at a temperature of from about 0° C. to about 100° C., in the presence of a catalytic amount of a catalyst comprising:
    (1) at least one Lewis acid halide of the formula $AlCl_mBr_n$ where m and n are individually integers of 0-3 and the sum of m+n is 3, and
    (2) a proton source,
  such that the isopropyl group of 2,4-dichlorocumene is preferentially transferred, as compared to the isopropyl group of 3,5-dichlorocumene, to the acceptor thereby forming a reaction product comprising the acceptor bearing said isopropyl group, 3,5-dichlorocumene and m-dichlorobenzene; and
  (b) separating 3,5-dichlorocumene from the said reaction product.

The process of this invention is advantageous not only because the 3,5-dichlorocumene is effectively separated and recovered from an isomeric mixture, but also because the process generates m-dichlorobenzene. This latter compound is a useful intermediate in the preparation of a wide variety of compounds having biological activity. 3,5-Dichlorocumene is also a useful intermediate in the preparation of similar compounds.

DETAILED DESCRIPTION OF THE INVENTION

Any mixture of 3,5- and 2,4-dichlorocumene can be employed in the practice of the present invention. One such mixture is the reaction product from the alkylation of a m-dihalobenzene such as m-dichlorobenzene. A representative alkylation procedure is taught by Dreisback, supra. A typical reaction product comprises a blend of 3,5- and 2,4-dichlorocumene, excess m-dichlorobenzene and relatively minor amounts of other unresolved materials. Another useful mixture is one obtained by distilling a typical alkylation reaction product, such as identified above, which leaves a blend consisting essentially of the isomers. As indicated hereinbefore, the mixture can contain essentially any combination of 3,5-dichlorocumene and 2,4-dichlorocumene but preferably the mixture contains at least a 1:1 weight ratio of 3,5-dichlorocumene to 2,4-dichlorocumene. A mixture containing at least a 3:2 weight ratio of 3,5-dichlorocumene to 2,4-dichlorocumene is more preferred and a mixture containing at least about a 3:1 weight ratio of 3,5-dichlorocumene to 2,4-dichlorocumene is especially preferred.

While one of the mixtures set forth above contains unreacted m-dichlorobenzene, which acts as a solvent for the dichlorocumenes, the use of a solvent in the practice of this invention is optional. In a typical procedure, no additional solvent is necessary as the hereinafter set forth isopropyl group acceptors can also act as a solvent for the dichlorocumenes.

The other materials found in the typical mixture employed as the starting material for the practice of this invention are the unconverted starting materials and by-products of the process used to prepare the blend of dichlorocumenes, such as disclosed in U.S. Pat. No. 4,059,642. These other materials are generally present in amounts less about 15 weight percent (based on the total weight of the mixture) and their effect on the practice of this invention is negligible.

Virtually any compound capable of combining with an isopropyl group under the conditions of this invention and essentially non-reactive with both the starting materials and products of this invention can be used as the isopropyl group acceptor. Typically, the acceptor is an aromatic compound such as benzene, toluene, monochlorobenzene, phenylbenzene (biphenyl), ethylbenzene, cumene, and other aromatics with similar Lewis basicity. Although this invention can be practiced with equal molar amounts of the acceptor and 2,4-dichlorocumene, preferably the invention is practiced with a molar excess of the acceptor. Such an excess promotes complete transalkylation of the isopropyl group from 2,4-dichlorocumene to the acceptor.

The mixture and acceptor are contacted at a temperature at which both are substantially liquid, and preferably completely liquid. Typically, a minimum temperature employed in the practice of this invention is about 0° C. and preferably about 20° C. A typical maximum temperature is about 100° C. and preferably about 90° C. The exact temperature employed in any given embodiment of this invention will vary with the species and amount of catalyst as well as with the species and amount of acceptor. Desirable results are obtained from the practice of this invention at relatively low temperatures (0° C.–10° C.) when an aluminum bromide-hydrogen bromide catalyst and benzene acceptor are used as well as when this invention is practiced at relatively high temperatures (80° C.–100° C.) when an aluminum chloride-hydrogen chloride catalyst and toluene acceptor are employed.

Pressure is critical to this invention only as it relates to temperature and thus this invention can be practiced at reduced, atmospheric or superatmospheric pressure.

The mixture and acceptor are contacted in the presence of a catalyst comprising at least one Lewis acid of the formula $AlCl_mBr_n$ where m and n are as previously defined and a proton source. The Lewis acid can be anhydrous or hydrated and contain small amounts of absorbed water, typically, those amounts absorbed through conventional handling techniques such as weighing, transferring, etc. Aluminum chloride ($AlCl_3$) and aluminum bromide ($AlBr_3$) are well-known in the art and thus are typically the Lewis acids of choice although the Lewis acids having both species of halide anion (e.g., m is one and n is two) perform well in this invention. These Lewis acids can be preformed or generated in situ.

In addition to the Lewis acid, the catalyst of this invention also requires the presence of a proton source. Any material capable of donating a proton to the reaction mechanism or operation of this invention, i.e., the preferential transfer of the isopropyl group from 2,4-dichlorocumene to the acceptor, can be used as the proton source. Typical proton sources include hydrogen chloride, hydrogen bromide, water, alcohols and other proton sources that are known to the art of Lewis acid catalysis. Hydrogen chloride, hydrogen bromide and small amounts of water are the preferred proton sources.

The catalysts of this invention can contain more than one Lewis acid as well as more than one proton source. Although the catalyst typically comprises only one Lewis acid, it is not uncommon to practice this invention in the presence of more than one proton source. This latter situation arises most frequently when hydrogen chloride or hydrogen bromide is used as the principal proton source. Generally, this invention is not practiced under anhydrous conditions and water need be present in only small amounts to serve as an effective proton source. As such, such processes have both the hydrogen chloride or bromide and water as a proton source although the hydrogen halide generally dominates the latter.

The catalyst of this invention is believed to be a complex formed from the combination of the Lewis acid and the proton source, e.g., $AlCl_3:HCl$. As such, a Lewis acid:proton source mole ratio of 1:1 is appropriate to the practice of this invention with an excess of either species neither significantly contributing nor impeding the invention. For reasons of convenience the invention is typically practiced with an excess of proton source, generally by sparging sufficient hydrogen chloride or hydrogen bromide into the reaction mixture to saturate it.

When water is the proton source, usually sufficient water is present in the hydrated form of the catalyst. While small additional amounts of water can be present, the adding of additional water is not usually necessary and is discouraged. Water in excess of the 1:1 mole ratio of Lewis acid:proton source as noted above, tends to destroy the catalytic activity and terminate the reaction. Normally, water which is inherently present in the feed, catalyst and the process system in general is usually sufficient to carry out the process.

A catalytic amount of catalyst (Lewis acid plus proton source) is required for the practice of this invention. Minimum amounts of catalyst will vary with other process parameters, such as temperature and species and amount of acceptor, but a typical amount is from about 0.1 to about 3 weight percent or more, based upon the combined weight of the 3,5- and 2,4-dichlorocumenes, and preferably about 2 weight percent.

In the practice of this invention, the isopropyl group of 2,4-dichlorocumene is preferentially transferred (or transalkylated) to an isopropyl group acceptor. This transfer thus forms two new compounds, namely the acceptor bearing the isopropyl group and m-dichlorobenzene. Typically, substantially all of the 2,4-dichlorocumene and acceptor are converted by transalkylation to these new compounds. The product mixture then comprises 3,5-dichlorocumene, acceptors bearing the isopropyl group and m-dichlorobenzene and these materials are easily separated by conventional separatory procedures, such as distillation. Typically, 3,5-dichlorocumene can be recovered from the product mixture in greater than 95 percent purity.

In one embodiment of this invention, a mixture of 3,5- and 2,4-dichlorocumene is contacted with about an equal volume of benzene at a temperature between about 20° C. and about 80° C. in the presence of a catalytic amount of an aluminum chloride-hydrogen chloride catalyst. The aluminum chloride is added and hydrogen chloride is sparged through the reaction mixture. The contacting is done with sufficient agitation to maintain the catalyst thoroughly dispersed throughout the reaction mixture over the course of the contact time. At the completion of the reaction period, substantially all of the 2,4-dichlorocumene has been converted to m-dichlorobenzene while substantially all of the 3,5-dichlorocumene remains unconverted. The product mixture comprises benzene, m-dichlorobenzene, cumene, and 3,5-dichlorocumene. Distillation of the product mixture yields 3,5-dichlorocumene in excess of 95 percent purity. m-Dichlorobenzene is also readily recoverable in high purity.

The following are illustrative embodiments of this invention. Unless noted to the contrary, all parts and percentages are by weight.

SPECIFIC EMBODIMENTS

The proton source of Examples 1–2 and Controls A–E was water. The exact amount of water present in these examples and controls is unknown but exemplary of the sources of this water is water absorbed by the starting materials, including the Lewis acid, and the water adhering to the process apparatus.

EXAMPLE 1

A mixture (352 g) comprising 3,5-dichlorocumene (63.1 percent), 2,4-dichlorocumene (28 percent) and other material (8.9 percent) was mixed with benzene (357 g) and aluminum chloride (6 g), the mixing done at room temperature. The mixture was then heated with stirring to 60° C. and there maintained for 90 minutes. The reaction mixture was then cooled to 30° C. and quenched with water (30 g). After hydrolysis of the aluminum chloride catalyst, the organic phase (674 g) was separated from the water and subjected to gas chromatographic analysis. The analysis showed the organic phase to be composed of:
  benzene: 51.8 percent
  cumene: 9.0 percent
  m-dichlorobenzene: 14.4 percent
  2,4-dichlorocumene: 0.6 percent
  3,5-dichlorocumene: 23.4 percent
  unresolved: 1.8 percent Distillation of the organic phase using a 10-plate column and a pressure of 10–40 mm Hg yielded 183 grams of a product which analyzed as:
  3,5-dichlorocumene: 97.6 percent
  2,4-dichlorocumene: 1.4 percent
  unresolved: 1.0 percent This example illustrates the efficacy of this invention for the separation of 3,5-dichlorocumene from an isomeric mixture of 3,5- and 2,4-dichlorocumene.

EXAMPLE 2

Benzene (78 g) was mixed with aluminum chloride (0.0098 mole). A mixture (78 g) of 2,4-dichlorocumene (38.6 percent), 3,5-dichlorocumene (58.8 percent) and other material (2.4 percent) was then added to the mixture of benzene and aluminum chloride. The resulting mixture was then heated to and maintained at 60° C. for 90 minutes at which time the mixture was sampled and the samples subjected to gas chromatographic analysis:
  benzene: 42.0 percent
  cumene: 12.2 percent
  m-dichlorobenzene: 14.7 percent
  2,4-dichlorocumene: 0.5 percent
  3,5-dichlorocumene: 29.1 percent
  unresolved: 1.5 percent This example as well as Example 1 demonstrates the efficacy of this invention in the presence of other materials.

COMPARISONS A–E

Example 2 was quintuplicated except that sulfuric acid, antimony pentachloride, ferric chloride, titanium chloride, and stannic chloride were sequentially substituted for the aluminum chloride. Samples taken and analyzed at like conditions under each of these controls revealed:
  benzene: 50.2 percent
  2,4-dichlorocumene: 19.3 percent
  3,5-dichlorocumene: 29.4 percent
  unresolved: 1.1 percent This demonstrates in these comparisons that essentially none of the 2,4-dichlorocumene was transalkylated with the available benzene.

EXAMPLE 3

3,5-Dichlorocumene (37.8 g, 0.2 mole), 2,4-dichlorocumene (9.5 g, 0.05 mole), benzene (78 g, 1.0 mole) and aluminum bromide (5.9 g, 0.022 mole) were combined in a 3-neck round bottom flask equipped with a hydrogen bromide sparger, mechanical stirrer, nitrogen-blanketed condenser and an ice-water cooling bath. The mixture was cooled to about 5° C. and then saturated with anhydrous hydrogen bromide by sparging for 5 minutes. The reaction mixture was maintained for approximately 1 hour at 0° C.–5° C. and subsequently analyzed by standard gas chromatography. The product mixture contained about:
  m-dichlorobenzene: 7.5 g
  3,5-dichlorocumene: 39.4 g
  2,4-dichlorocumene: 0.6 g This example demonstrates the practice of this invention at relatively low temperatures.

EXAMPLE 4

3,5-Dichlorocumene (47.3 g, 0.25 mole), 2,4-dichlorocumene (9.5 g, 0.05 mole), toluene (92 g, 1.0 mole) and aluminum chloride (3 g, 0.022 mole) were combined in a 3-neck round bottom flask equipped with a hydrogen chloride sparger, mechanical stirrer, nitrogen-blanketed condenser and a heating mantle. The mixture was saturated with anhydrous hydrogen chloride by sparging for 5 minutes. The reaction mixture was then heated to about 90° C. and held at that temperature for approximately 1 hour. Subsequent analysis by standard gas chromatography showed the mixture contained about:
  m-dichlorobenzene: 10.3 g
  3,5-dichlorocumene: 44.6 g
  2,4-dichlorocumene: Not detected This example demonstrates the use of both a relatively high temperature and toluene as an acceptor.

EXAMPLE 5

To a mixture of m-dichlorobenzene (161 g, 1.1 mole), 3,5-dichlorocumene (119 g, 0.63 mole), 2,4-dichlorocumene (31.3 g, 0.165 mole) and aluminum chloride (19 g, 0.15 mole), saturated with anhydrous hydrogen bromide was added biphenyl (54 g, 0.35 mole). The reaction mixture was heated to about 40° C. and there held for about 6 hours after which an additional 23 g (0.15 mole) of biphenyl was added. The reaction was allowed to continue at 40° C. for an additional 16 hours. Subsequent analysis of the reaction product by standard gas chromatography showed the product contained about:
  m-dichlorobenzene: 180 g
  3,5-dichlorocumene: 120 g
  2,4-dichlorocumene: 4.5 g This example demonstrates that the presence of a solvent, here m-dichlorobenzene, does not have a deleterious effect upon the results. This example also demonstrates the use of a Lewis acid having both species of halide anion, here generated in situ. This example further demonstrates the use of biphenyl as an isopropyl group acceptor.

EXAMPLE 6

To a mixture of m-dichlorobenzene (207 g, 1.41 mole), 3,5-dichlorocumene (72 g, 0.38 mole), 2,4-dichlorocumene (17.8 g, 0.095 mole) and aluminum chloride (12 g, 0.09 mole) saturated with anhydrous hydrogen bromide was added benzene (74 g, 0.95 mole). The reaction mixture was stirred at about 25° C. and after 1½ hours of reaction time, analysis by standard gas chromatography showed the product mixture contained about:
  m-dichlorobenzene: 231 g
  3,5-dichlorocumene: 74 g
  2,4-dichlorocumene: 1.5 g The negligible differences reported between the starting weight and closing weight of the 3,5-dichlorocumene in some of the above examples is within experimental error.

Although the invention has been described in considerable detail by the preceding examples and controls, such detail is for the purpose of illustration only and many variations and modifications can be made by one skilled in the art without departing from the spirit and scope of the appended claims.

What is claimed is:

1. A process for separating 3,5-dichlorocumene from a starting mixture comprising 3,5-dichlorocumene and 2,4-dichlorocumene, which comprises:
    (a) contacting the said starting mixture with at least one aromatic isopropyl group acceptor, which is essentially non-reactive with the starting materials or products, at a temperature of from about 0° C. to about 100° C., in the presence of a catalytic amount of a catalyst comprising:
        (1) at least one Lewis acid compound of the formula $AlCl_mBr_n$ where m and n are individually integers of 0–3 and the sum of m+n is 3, and
        (2) a proton source,
    such that the isopropyl group of 2,4-dichlorocumene is preferentially transferred, as compared to the isopropyl group of 3,5-dichlorocumene, to the acceptor thereby forming a reaction product comprising the acceptor bearing said isopropyl group, 3,5-dichlorocumene and m-dichlorobenzene; and
    (b) separating 3,5-dichlorocumene from the said reaction product.

2. The process of claim 1 wherein the 3,5-dichlorocumene and 2,4-dichlorocumene in the starting mixture are present at a 3,5-dichlorocumene:2,4-dichlorocumene weight ratio of at least about 1:1.

3. The process of claim 2 wherein the 3,5-dichlorocumene and 2,4-dichlorocumene in the starting mixture are present in the mixture at a 3,5-dichlorocumene:2,4-dichlorocumene weight ratio of at least about 3:1.

4. The process of claim 3 wherein the proton source is hydrogen chloride, hydrogen bromide or a trace amount of water.

5. The process of claim 4 wherein the catalyst is present in an amount of from about 0.1 to about 3 weight percent based upon the combined weight of the 3,5- and 2,4-dichlorocumenes.

6. The process of claim 5 wherein the catalyst is present in an amount of about 2 weight percent based upon the combination weight of the 3,5- and 2,4-dichlorocumenes.

7. The process of claim 6 wherein the acceptor is benzene, toluene, monochlorobenzene, phenylbenzene, ethylbenzene or cumene.

* * * * *